United States Patent [19]

Kida et al.

[11]  4,225,585

[45]  Sep. 30, 1980

[54] FUNGICIDAL AND BACTERICIDAL COMPOSITIONS AND METHOD FOR PROTECTING PLANTS BY USE THEREOF

[75] Inventors: Takao Kida, Yokosuka; Zuisho Terahara, Yokohama; Toshiro Shida, Yokohama; Hiroshi Mizuno, Yokohama; Yoshiyuki Takahara, Tokyo; Yoshiteru Hirose, Kamakura, all of Japan

[73] Assignee: Ajinomoto Company, Incorporated, Tokyo, Japan

[21] Appl. No.: 908,750

[22] Filed: May 23, 1978

[51] Int. Cl.² .................. A01N 9/00; A61K 31/71; A61K 35/00
[52] U.S. Cl. ..................................... 424/114; 424/181
[58] Field of Search ............................. 424/181, 114

[56] References Cited

U.S. PATENT DOCUMENTS 3,207,750  9/1965  DeBoer et al. ................ 260/211.5

OTHER PUBLICATIONS

Kirk–Othmer, Encyclopedia of Chemical Technology, vol. 2, 3rd Ed., 1978, pp. 974, 975 & 984.
Frear, Chemistry of the Pesticides, received U.S. Pat. Office 7/18/55, 306–307.
Tanaka et al., C. A., vol. 56, (1962), 14881g.
Tanaka et al., C. A., vol. 61, (1964), 6227h.
Yunsten et al., C. A., vol. 54, (1960), 3428c.

*Primary Examiner*—Allen J. Robinson
*Attorney, Agent, or Firm*—Oblon, Fisher, Spivak, McClelland & Maier

[57] ABSTRACT

Fungicidal compositions for agricultural and horticultural use are provided which contain as an active ingredient thereof the antibiotics angustmycin A or angustmycin C. They exhibit excellent protective effects against attack by plant disease fungi or bacteria, have no phytotoxicity and cause no pollution in the environment. A method for protecting plants by the use thereof is also provided.

2 Claims, No Drawings

Fungicidal and Bactericidal Compositions and Method for Protecting Plants by Use Thereof

BACKGROUND OF THE INVENTION

1. Field of the Invention

The present invention relates to fungicidal compositions or agents which exhibit excellent fungicidal effects and in which there is no risk of pollution being caused thereby; and to a method for the use thereof. More particularly, the present invention relates to fungicidal compositions for agricultural and horticultural use which comprise or consist of fungicidal amount of a angustmycin A or angustmycin C and a carrier for agricultural and horticultural formulation.

2. Description of the Prior Art

The term "fungicidal composition or agent" as used in the present specification and claims, is meant to include a bactericidal composition or agent besides its literal sense.

Various attempt to utilize anbiotics or metabolic products of microorganisms as agricultural and horticultural fungicides have been made hitherto, and as the result, some good results have been obtained. As antibiotics for agricultural and horticultural use, blasticidis S and kasugamycin have been practically used to control rice blast; polymyxin to control alternaria leaf spot of apple, powdery mildew of vegetable plants and sheath blight of rice; validamycin to control sheath blight of rice; novobiocin to control bacterial canker of tomatos; streptomycin for medical use and oxytetracycline to control citrus melanose; and cycloheximide to control downy mildew of onion.

Most of these antibiotics have effect against specific disease causative organisms for agricultural plants and their applying amount per area is small, and their remaining period in crops and soils is relatively short. However, continuous use of these anbiotics in the agricultural and horticultural field has caused the emergence of resistant strains of pathogenic bacteria and countermeasures have become necessary. Also, use of the medically employed antibiotics as agricultural and horticultural fungicides is prohibited or restricted, as seen in the case of chloramphenicol. Therefore, development of a novel agricultural and horticultural fungicides to be used as substitute for the antibiotic chemical used hitherto has been eagerly desired. No antibiotic chemical which is effective particularly against anthracnose, gray mold and bacterial spot of vegetable plants has been developed yet.

SUMMARY OF THE INVENTION

As the result of having extensively researched the matter with a view towards developing antibiotic chemicals which have not been practically used as medicine and which have both a high preventive effect even against plant diseases just mentioned and high safety, it has now been found that the nucleoside antibiotics, angustmycins A and C which may be isolated from the culture broth of Streptomyces hygroscopicus exhibit excellent preventive effect against numerous plant diseases such as cucumber anthracnose, cucumber bacterial spot, cucumber powdery mildew, rice blast, rice leaf blight, citrus melanose and others, and that they have no phytotoxicity to any kind of plant and cause no risk of pollution in the environment.

DETAILED DESCRIPTION OF THE PREFERRED EMBODIMENT

Angustmycins A and C, each of which is an active ingredient of the present fungicidal composition for agricultural and horticultural use may be isolated from the culture broth of angustmycins A and C producing bacterium belonging to the genus Streptomyces hydroscopicus by a well-known conventional process.

It is known that angustmycins A and C exhibit specific antibacterial activity against gram-positive organisms and mycobacteria in vitro (H. Yüntsen et al; J. Antibiot. 7, A, 113 (1954)), and they have specific antitumor activity against Walker adenocarcinoma 256 in rats (N. Tanaka et al; J. Antibiot., 14, A, 98 (1961)). Also, J. S. Evans et al have reported in Antibiot. and chemoth 9, 675 (1959) that angustmycin C is extremely nontoxic substance. However, neither angustomycins A nor C has been practically used as medicine and there was made no report regarding antibacterial or antifungal activity of these two antibiotics against disease causative organisms for agricultural plants and regarding their application as agricultural fungicides.

It is surprising that angustmycins A and C have excellent preventive effect against cucumber bacterial spot caused by Pseudomonas lachrymans and cucumber anthracnose caused by Colletotrichum lagenarium which are difficult to control with the antibiotic chemical hitherto used.

The active ingredient of the present invention is especially useful in controlling the following fungi (and bacteria) which tend to attack food crops: Xanthomonas oryzae, the causative organism of bacterial leaf blight; Xanthomonas citri, the causative organism of citrus canker; Colletotrichum lagenarium, the causative organism of cucumber anthracnose; Phytophthora parasitica, the causative organism of cucumber phytophthora rot; Pseudomonas lachrymans, the causative organism of cucumber bacterial spot; Phytophthora infestans, the causative organism of tomato late blight; and others.

The active ingredient of the fungicides of the present invention may be directly applied to the fungus-susceptible plant surface, or it may be applied thereto in any formulation such as granules, dusts, emulsifiable concentrates, wettable powders, pastes, oil agents, aerosols, fogs or fumigants with suitable solid carriers, liquid carriers, emulsifying and dispersing agents and the like, as in the case of the usual formulations well known in the art. Examples of these carriers include clay, kaolin, bentonite, acidic terra abla, diatomaceous earth, calcium carbonate, nitrocellulose, starch, acacia, carbon dioxide, Freon and the like. Also, while not required, the active ingredient of the invention may be suitably compounded with those auxiliary agents which are usually employed in the formulation of fungicides, e.g., surface active agents which serve as a spreading, dispersing and emulsifying agent. Examples of such surface active agents are soap, higher alcohol sulfate, alkyl sulfonate, alkylaryl sulfonate, quaternary ammonium salts, polyalkylene oxide and the like. The preferred concentration of the active ingredient in the fungicidal composition is about 0.1–50% by weight. However, the concentration may be suitably varied in accordance with the intended use of the fungicide.

The amount of the fungicidal compositon to be applied may be varied according to such factors as the formulation of the composition, the class of the active ingredient or the concentration of the active ingredient in the composition. It is usually applied at the rate of about 5 grams per 10 ares to 500 grams per 10 ares, and preferably 20 grams per 10 ares to 100 grams per 10 ares, calculated as the active ingredient. However, greater amounts may be applied, if desired.

The active ingredient of this invention may also be employed in admixture with herbicides, insecticides, other fungicides, soil conditioners, and fertilizers such as urea, ammonium sulfate, ammonium phosphates, potassium salts and the like.

Next, examples of the preparation of the invention fungicidal composition for agricultural and horticultural use will be given. In the examples the parts are on a weight basis.

PREPARATION EXAMPLE 1

50 Parts of angustmycin A, 44 parts of white carbon, 2 parts of sodium lignin sulfonate and 4 parts of polyoxyethylene laurylether were mixed together and milled to obtain 100 parts of wettable powder.

PREPARATION EXAMPLE 2

50 Parts of angustmycin C, 10 parts of polyoxyethylene nonylphenol ether, 10 parts of methanol and 30 parts of water were mixed together to obtain 100 parts of emulsifiable concentrate.

Next, the effects of preventing the various plant disease fungi by use of the invention fungicidal composition for agricultural and horticultural use will be specifically illustrated.

APPLICATION EXAMPLE 1

Test for evaluating the effectiveness of preventing cucumber bacterial spot.

Cucumber seeds (variety "Sagami Hanjiro") were planted, three seeds being planted per seed-bed, and they were grown in a greenhouse constructed of glass. This experiment was performed as three-repeated cultivations. An aqueous dilution of an emulsifiable concentrate prepared according to Preparation Example 2 was sprayed on the cucumber seedlings in the three-leaved stage with a shoulder-borne sprayer, ensuring that both sides of the leaves were throughly wetted.

Pathogenic bacteria causing bacterial spot in cucumber (Pseudomonas lachrymans) which had been cultured for 48 hours at 35° C. in Wakimoto culture medium containing potato, sucrose, peptone, and salts, were taken into sterilized water, and then carborundum (#500) was added to form a bacterium suspension containing 1% carborundum.

The bacterium suspension was sprayed on the cucumber seedings in an amount of $10^5$ bacteria per 1 g of cucumber leaf by a spray gun to effect inoculation. The so treated seedings were then placed in an inoculation box of 23° C. and relative humidity of above 95% to cause the diseases.

Five days after inoculation, the number of disease lesions which appeared on leaves of the plants was counted, and the preventive value was calculated according to the following formula:

$$\text{Preventive value (\%)} = \left(1 - \frac{\text{Number of disease lesions of treated leaf}}{\text{Number of disease lesions of untreated leaf}}\right) \times 100$$

The results obtained are shown in Table 1.

TABLE I

| Compound tested | Concentration (ppm) in sprayed composition | Preventive value (%) | Phytotoxicity* |
|---|---|---|---|
| Angustmycin A | 100 | 60 | — |
|  | 250 | 80 | — |
|  | 500 | 95 | — |
| Angustmycin C | 100 | 65 | — |
|  | 250 | 85 | — |
|  | 500 | 100 | — |
| Basic copper chloride | 1,000 | 70 | — |
| Untreated plant |  | 0 |  |

*No phytotoxicity was observed.

APPLICATION EXAMPLE 2

Test for evaluating the effectiveness of preventing cucumber anthracnose.

Cucumber seeds (Variety: "Sagami Hanjiro") were planted in synthetic resin pots of 6 cm in diameter, one seed being planted per pot and were grown in a greenhouse.

On the cucumber seedlings 1~2 leaved stage grown after 2 weeks, was sprayed the diluted aqueous solution of a wettable powder prepared according to Preparation Example 1 at a rate of 50 ml per pot and then dried.

Spores of a pathogenic bacterium causing anthracnose in cucumber (Colletotrichum lagenarium) which had been cultured for 10 days at 25° C. in an agar slant culture medium of sweet corn, were taken into sterilized water. In inoculation box placed in fungitron, a spore suspension containing 50 spores counted using a microscope of 150 magnification was prepared and sprayed on the plants by a spray gun to effect inoculation.

The so treated plants were allowed to stand in the dark at a relative humidity of 90% and a temperature of 25° C. for 2 days and then transferred into the greenhouse. After 2 days, the number of disease lensions per leaf was counted, and the preventive value was calculated according to the formula shown in Application Example 1.

The results obtained are shown in Table 2.

TABLE 2

| Compound tested | Concentration (ppm) in sprayed composition | Preventive value (%) | Phytotoxicity |
|---|---|---|---|
| Angustmycins A and C mixture (1:1) | 250 | 90 | — |
|  | 500 | 95 | — |
| "Daisen" | 1,000 | 98 | — |

"Daisen": trade name, product of Kumiai Chemical Industrial Co., Ltd., wettable powder containing zinc ethylene-bis (dithiocarbamate).

APPLICATION EXAMPLE 3

Test for evaluating the effectiveness of preventing rice leaf blight.

In each of a number of synthetic resin pots having a diameter of 6 cm, 10 stalks of rice (variety: "Jukkoku") were planted in a greenhouse and in the four to five-stage, a diluted aqueous solution of a emulsifiable concentrate prepared according to the Preparation Example 2 was sprayed on the plants at the rate of 40 ml per pot with a sprayer.

After the sprayed chemical was dried, cells of a pathogenic bacterium causing leaf blight on rice (Xanthomonas oryzae) which had been cultivated in a bacterial leaf blight culture medium at 27° C. for 3 days were suspended in water and inoculated with a needle to the highest and the second highest leaves of the rice plant. In two or three weeks after inoculation the leaves were infected with the foregoing fungus. The length of the disease lesions per stalk was then measured, and the preventive value was calculated as follows:

$$\text{Preventive value (\%)} = \left(1 - \frac{\text{Length of disease lesions of treated leaf}}{\text{Length of disease lesions of untreated leaf}}\right) \times 100$$

The results obtained are shown in Table 3.

TABLE 3

| Compound tested | Concentration (ppm) in sprayed composition | Preventive value (%) | Phyto-toxicity |
|---|---|---|---|
| Angustmycins A and C mixture | 250 | 85 | — |
| | 500 | 95 | — |
| (1:1) "Phenazine"* | 125 | 92 | — |

*Phenazine: trade name, product of Kumiai Chemical Industrial Co., Ltd., wettable powder containing phenazine 5-oxide.

What is claimed as new and intended to be covered by letters patent is:

1. A method for combatting fungi and bacteria diseases on plants which comprises applying to the plant disease fungi and bacteria on rice or vegetable plants a fungicidal or bactericidal amount of angustmycin A or angustmycin C wherein said plant disease fungi or bacteria are the causative organism of rice leaf blight, rice blast, cucumber bacterial spot, cucumber anthracnose, cucumber phytophthora rot, cucumber powdery mildew, citrus melanose, citrus canker or tomato late blight.

2. The method of claim 1, wherein said plant disease fungi or bacteria are the causative organisms of rice leaf blight, cucumber bacterial spot, or cucumber anthracnose.

* * * * *